United States Patent [19]

Gumbrecht et al.

[11] Patent Number: 5,376,255
[45] Date of Patent: Dec. 27, 1994

[54] GAS SENSOR

[75] Inventors: Walter Gumbrecht, Herzogenaurach; Wolfgang Schelter, Uttenreuth; Siegrun Lang, Erlangen, all of Germany

[73] Assignee: Siemens Aktiengesellschaft, Munich, Germany

[21] Appl. No.: 119,602

[22] Filed: Sep. 10, 1993

[30] Foreign Application Priority Data

Sep. 14, 1992 [DE] Germany ............... 4230690

[51] Int. Cl.$^5$ ............................................. G01N 27/26
[52] U.S. Cl. ..................... 204/426; 204/414; 204/415; 204/418; 204/433; 204/435
[58] Field of Search .............. 204/433, 435, 416, 418, 204/414, 426, 415

[56] References Cited

U.S. PATENT DOCUMENTS 3,649,505  3/1972  Strickler et al. ............. 204/195
4,874,500  10/1989  Madou et al. ............. 204/416
5,183,549  2/1993  Joseph et al. ............. 204/435

OTHER PUBLICATIONS

Shimada, K. et al., "Application of catheter-tip i.s.f.e.t. for continuous in vivo measurement," *Medical & Biological Engineering & Computing*, vol. 18 (1980), pp. 741–745.

Hu, B. et al., "Carbon Dioxide Gas-Sensing Electrode Base On A pH-Isfet With Back-Side Contacts," *Sensors and Actuators*, vol. 17 (1989), pp. 275–278.

Tsukada, K. et al., "An Integrated Chemical Sensor with Multiple Ion and Gas Sensors," *Sensors and Actuators B*, vol. 2 (1990), pp. 291–295.

Göpel, W. et al., "Sensors: A Comprehensive Survey," vol. 2, *VCH Verlagsgesellschaft mbH*, Weinheim 1991, pp. 488 and 489.

Cammann, Karl, "Das Arbeiten mit ionenselektiven Elektroden," *Springer-Verlag Berlin*, Heidelberg 1977, pp. 95–100.

*Primary Examiner*—John Niebling
*Assistant Examiner*—Bruce F. Bell
*Attorney, Agent, or Firm*—Kenyon & Kenyon

[57] ABSTRACT

A planar gas sensor, in particular a $pCO_2$ or $pO_2$ sensor, has the following components: a pH sensor located on a flat substrate, or at least one noble metal electrode located on the substrate; a reference electrode adjacent to the pH sensor or noble metal electrode; an electrolyte layer, covering the reference electrode and the pH sensor or noble metal electrode, which is delimited by a first polymer structure; and a layer of hydrophobic material, covering the electrolyte layer and a surface region of the substrate outside the first polymer structure, which is delimited by a second polymer structure.

20 Claims, 1 Drawing Sheet

GAS SENSOR

BACKGROUND OF THE INVENTION

1. Field of the Invention

The invention relates to a planar gas sensor, in particular a $pCO_2$ or $pO_2$ sensor.

2. Description of Related Art

The partial pressure of carbon dioxide ($pCO_2$) in aqueous media, for example in blood, is usually determined according to the Severinghaus principle, i.e. by means of a sensor based on a pH-sensitive glass electrode (cf. W. Göpel, J. Hesse, and J. N. Zemel (eds.), "Sensors: A Comprehensive Survey," vol. 2 ("Chemical and Biochemical Sensors"), VCH Verlagsgesellschaft mbH, Weinheim 1991, pp. 488–489). The pH sensor is located—in combination with a Ag/AgCl reference electrode—in an unbuffered NaCl/NaHCO$_3$ solution. This arrangement is isolated from the measuring solution by a membrane made of a hydrophobic material, for example silicone rubber. Carbon dioxide—unlike ions—can diffuse through this membrane and change the pH value of the internal solution according to the equation:

$$CO_2 + H_2O \rightleftharpoons H_2CO_3 \rightleftharpoons HCO_3^- + H^+$$

Since the $Cl^-$ concentration of the internal solution remains constant, the Ag/AgCl electrode delivers a constant reference potential (cf. for example K. Cammann, "Das Arbeiten mit ionenselektiven Elektroden" [Working with ion-selective electrodes], 2nd ed., Springer-Verlag Berlin, Heidelberg 1977, pp. 95–96).

Attempts have been made to transfer the Severinghaus principle to planar-technology arrangements with pH-sensitive FETs (field effect transistors); however, none of these arrangements has so far been developed to the production stage. For example, a Severinghaus-type $pCO_2$ sensor in the form of a catheter-tip is known (see "Med. & Biol. Eng. & Comput.," vol. 18 (1980), pp. 741–745). For this purpose a pH-ISFET, i.e. a pH-sensitive ISFET (ion-sensitive field effect transistor) is located at the tip of a thin nylon tube together with a Ag/AgCl electrode. In another $CO_2$ sensor based on the Severinghaus principle, a pH-ISFET is combined with a temperature-sensitive diode on a chip (see "Sensors and Actuators," vol. 17 (1989), pp. 275–278). This sensor has Ag/AgCl wire as the reference electrode, which is not integrated on the chip (hybrid arrangement).

Also known is an integrated chemical sensor with multiple ion and gas sensors arranged on a chip, that has a Severinghaus-type $pCO_2$ sensor (see "Sensors and Actuators B," vol. 2 (1990), pp. 291–295). The $pCO_2$ sensor has an ISFET (with a Si$_3$N$_4$ gate) as the internal pH sensor, and a Ag/AgCl reference electrode; the pH-ISFET and reference electrode are surrounded by a polyimide micropool. Located in this micropool is an electrolyte gel consisting of polyvinyl alcohol, NaCl, and NaHCO$_3$. The electrolyte gel is covered by a gas-permeable silicone rubber membrane with a thickness of between 50 and 100 μm. When the sensor is put into service, the electrolyte layer absorbs water vapor and swells, putting a mechanical load on the silicone membrane above it. However, since this membrane is attached to the wall of the polyimide micropool only at the edge (a few μm thick), long-term sealing and covering of the electrolyte is not guaranteed.

SUMMARY OF THE INVENTION

Accordingly, it is an object of the invention to provide a planar gas sensor, in particular a $pCO_2$ or $pO_2$ sensor, in which long-term operability is guaranteed, and that can be series-produced.

This is achieved, according to the invention, by a gas sensor having the following features:

A pH sensor located on a flat substrate, or at least one noble metal electrode located on the substrate;

A reference electrode adjacent to the pH sensor or noble metal electrode;

An electrolyte layer, covering the reference electrode and the pH sensor or noble metal electrode, which is delimited by a first polymer structure; and A layer of hydrophobic material, covering the electrolyte layer and a surface region of the substrate outside the first polymer structure, which is delimited by a second polymer structure.

BRIEF DESCRIPTION OF THE DRAWINGS

FIG. 1b is a planar view of the planar gas sensor illustrated in FIG. 1a.

DETAILED DESCRIPTION OF THE INVENTION

Figure 1A:
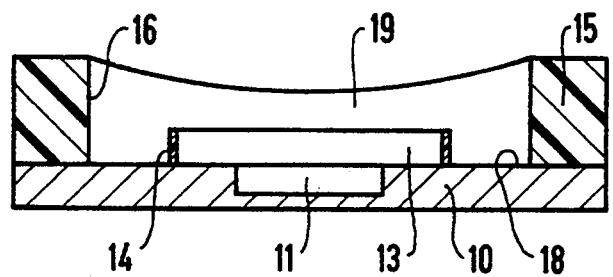
FIG. 1a is a cross-sectional view of a planar gas sensor in accordance with the invention.

The gas sensor according to the invention is based on either a pH sensor or at least one noble metal electrode, combined in each case with a reference electrode. In the case of a pH sensor, the gas sensor is used to determine carbon dioxide and similar gases; in the case of a noble metal electrode, the gas sensor determines oxygen. The pH sensor can be a pH-sensitive electrode, for example an IrO$_2$ electrode, that is arranged on an insulating substrate such as aluminum oxide or quartz. Preferably the pH sensor is a pH-ISFET that is located on a semiconductor substrate such as silicon. The noble metal electrode is preferably made of platinum. If only one noble metal electrode is present, the reference electrode then acts simultaneously as the counterelectrode; otherwise a second noble metal electrode is used as the counterelectrode. The noble metal electrodes are configured as thin films.

The reference electrode, which is arranged on an insulated substrate, preferably consists of a Ag/AgCl electrode, manufactured for example as a monolithic structure. With a $pO_2$ sensor the reference electrode is in fact exclusively a Ag/AgCl electrode. With a $pCO_2$ sensor and with sensors for gases similar to carbon dioxide, the reference electrode can also be a flat noble metal electrode, in particular one made of platinum; a reference electrode of this type is redox-sensitive.

Located on the combination of the pH sensor or noble metal electrode and the reference electrode is an electrolyte layer delimited by a first polymer structure. This is, for example, a ring of polymer material that surrounds the pH sensor or noble metal electrode and the reference electrode. This ring is produced by structuring a layer of the polymer material, forming what is called an "internal pool," which has a diameter of, for example, approximately 350 μm; this internal pool is then filled with electrolyte. A corresponding procedure—i.e. structuring a layer of polymer material—is used to generate a second polymer structure that surrounds the first structure. This forms an "outer pool" which has, for example, a diameter of approximately 600 μm.

This outer pool is filled with a solution of a hydrophobic material to produce a layer of hydrophobic material that covers the electrolyte layer in a fluid-tight manner.

However, the layer of hydrophobic material covers not only the electrolyte layer—i.e. the arrangement consisting of the pH sensor or noble metal electrode and the reference electrode, including the first polymer structure—but also the surface region of the substrate lying between the two polymer structures. The hydrophobic membrane is firmly anchored to the substrate surface over a large area, generally greater than 100 $\mu$m (corresponding to the spacing between the two polymer structures). This guarantees very good sealing of the electrolyte, especially when a silicon substrate covered with a thin $SiO_2$ layer is used, and when the hydrophobic membrane is made of polysiloxane, since polysiloxane adheres very well to $SiO_2$.

The first polymer structure preferably has a height of 1 to 10 $\mu$m, but it can also be higher, in particular up to 30 $\mu$m high; the second polymer structure preferably has a height of 10 to 30 $\mu$m, and is generally approximately 30 $\mu$m high. The width of the first polymer structure is preferably 10 to 50 $\mu$m, and the spacing between the first and the second polymer structure is preferably 50 to 200 $\mu$m. The polymer structures are designed, in particular, in a circular shape, but can, for example, also have a square or rectangular shape. The material used for the two polymer structures is preferably polyimide, but other structurable polymer materials are also possible, such as polybenzoxazole.

The electrolyte layer generally contains a hydrogel. Polyvinyl pyrrolidone (PVP) is preferably used as the hydrogel, but other hydrophilic polymers are also possible, such as polyvinyl alcohol (PVA) and polymeric 2-hydroxyethyl methacrylate (pHEMA). In the case of a $pCO_2$ sensor, the electrolyte layer additionally contains a hydrogencarbonate, in particular sodium hydrogencarbonate. When a Ag/AgCl electrode is present as a reference electrode, the electrolyte then has a chloride, in particular potassium chloride; in the case of a noble metal electrode it has a redox buffer system such as $Fe^{2+}/Fe^{3+}$, in particular in the form of $K_4[Fe(CN)_6]/K_3[Fe(CN)_6]$.

The layer of hydrophobic material preferably consists of polysiloxane in the form of silicone or silicone rubber. The advantage of this material is that it adheres very well to materials such as $SiO_2$ and $Si_3N_4$, thus guaranteeing that the electrolyte (which is swollen or liquid when the gas sensor is operating) is reliably enclosed and sealed.

The gas sensor according to the invention is generally used with aqueous media, but can also be used to sense moist flows of gas. The gas sensor according to the invention can be used not only as a $pO_2$ sensor but also preferably as a $pCO_2$ sensor, i.e. to determine carbon dioxide. Since a gas sensor of this type has a pH sensor, however, in principle it can be used to determine any gas in which hydrogen ions are produced or captured upon introduction into aqueous solutions, i.e. that causes a change in pH in the electrolyte. Such gases include, in addition to carbon dioxide ($CO_2$), in particular ammonia ($NH_3$), sulfur dioxide ($SO_2$), nitrogen dioxide ($NO_2$), hydrogen fluoride (HF), hydrogen sulfide ($H_2S$), and hydrocyanic acid or hydrogen cyanide (HCN).

Figure 1B:
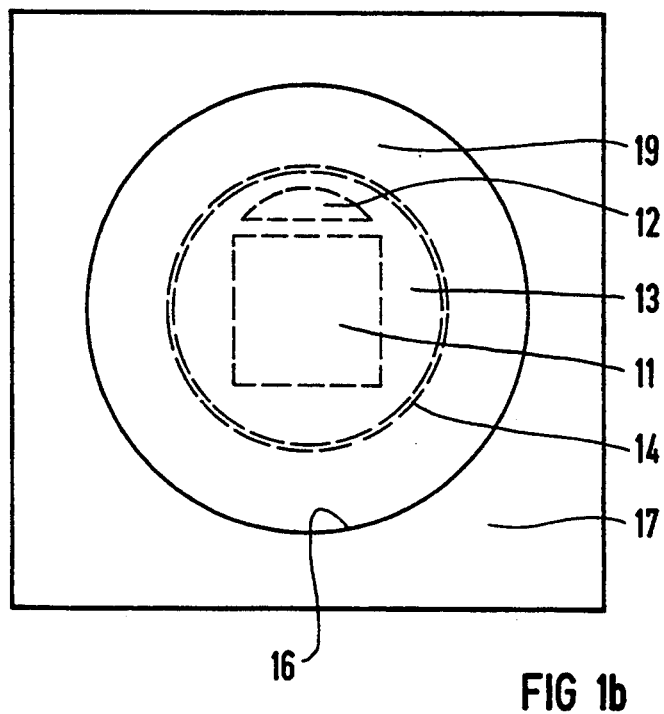

The invention will now be explained further with reference to FIG. 1, which depicts—in section (a) and in plan view (b)—an embodiment of the planar gas sensor according to the invention.

Arranged on a flat substrate 10, in particular a silicon substrate, is a pH sensor 11, in particular a pH-ISFET, adjacent to which is a reference electrode 12. The pH sensor 11 and reference electrode 12 are covered by an electrolyte layer 13 that is delimited by an annular polymer structure 14; i.e. electrolyte layer 13 is located in the space inside polymer structure 14. Annular polymer structure 14 is surrounded by a second polymer structure 15 in the form of a polymer layer 17 having a hole 16. The space inside polymer structure 15 is filled with a hydrophobic material; i.e. electrolyte layer 13 and a surface region 18 of substrate 10 located outside polymer structure 14 are covered with a layer 19 of hydrophobic material. This layer 19 is thus delimited by polymer structure 15.

What is claimed is:

1. A planar gas sensor comprising:
   A substantially flat substrate;
   A pH sensor or at least one noble metal electrode located on the substrate;
   A reference electrode adjacent to the pH sensor or noble metal electrode;
   An electrolyte layer, covering the reference electrode and the pH sensor or noble metal electrode;
   A first polymer structure which delimits the electrolyte layer;
   A layer of hydrophobic material, covering the electrolyte layer and a surface region of the substrate outside the first polymer structure; and
   A second polymer structure which delimits the layer of hydrophobic material.

2. The gas sensor according to claim 1 wherein the pH sensor is a pH-sensitive ion-sensitive field effect transistor.

3. The gas sensor according to claim 1 wherein the first polymer structure has a height of 1 to 10 $\mu$m, and the second polymer structure has a height of 10 to 30 $\mu$m.

4. The gas sensor according to claim 2 wherein the first polymer structure has a height of 1 to 10 $\mu$m, and the second polymer structure has a height of 10 to 30 $\mu$m.

5. The gas sensor according to claim 1 wherein the first polymer structure has a width of 10 to 50 $\mu$m, and which defines a spacing between the first and second polymer structures of from 50 to 200 $\mu$m.

6. The gas sensor according to claim 2 wherein the first polymer structure has a width of 10 to 50 $\mu$m, and which defines a spacing between the first and second polymer structures of from 50 to 200 $\mu$m.

7. The gas sensor according to claim 3 wherein the first polymer structure has a width of 10 to 50 $\mu$m, and which defines a spacing between the first and second polymer structures of from 50 to 200 $\mu$m.

8. The gas sensor according to claim 4 wherein the first polymer structure has a width of 10 to 50 $\mu$m, and which defines a spacing between the first and second polymer structures of from 50 to 200 $\mu$m.

9. The gas sensor according to claim 1 wherein the first and second polymer structures are polyimide.

10. The gas sensor according to claim 2 wherein the first and second polymer structures are polyimide.

11. The gas sensor according to claim 3 wherein the first and second polymer structures are polyimide.

12. The gas sensor according to claim 4 wherein the first and second polymer structures are polyimide.

13. The gas sensor according to claim 5 wherein the first and second polymer structures are polyimide.

14. The gas sensor according to claim 1 wherein the electrolyte layer contains a hydrogel.

15. The gas sensor according to claim 14 wherein the hydrogel is polyvinyl pyrrolidone.

16. The gas sensor according to claim 14 wherein the hydrogel contains a hydrogencarbonate.

17. The gas sensor according to claim 1 wherein the layer of hydrophobic material consists of polysiloxane.

18. The gas sensor according to claim 2 wherein the layer of hydrophobic material consists of polysiloxane.

19. The gas sensor according to claim 1 wherein the reference electrode is a Ag/AgCl electrode.

20. The gas sensor according to claim 2 wherein the reference electrode is a Ag/AgCl electrode.

* * * * *